(12) United States Patent
Cooper et al.

(10) Patent No.: US 7,462,242 B2
(45) Date of Patent: Dec. 9, 2008

(54) MISTING APPARATUS FOR ELECTROSTATIC APPLICATION OF COATING MATERIALS TO BODY SURFACES

(75) Inventors: Steven C. Cooper, Athens, GA (US); Troy H. Cooper, Addison, TX (US)

(73) Assignee: Mystic Tan, Inc., Farmers Branch, TX (US)

( * ) Notice: Subject to any disclaimer, the term of this patent is extended or adjusted under 35 U.S.C. 154(b) by 422 days.

(21) Appl. No.: 10/873,838

(22) Filed: Jun. 21, 2004

(65) Prior Publication Data

US 2005/0281957 A1    Dec. 22, 2005

(51) Int. Cl.
- B05B 5/025    (2006.01)
- B05B 1/28    (2006.01)
- A45D 44/00    (2006.01)
- A61M 35/00    (2006.01)
- A61H 33/06    (2006.01)

(52) U.S. Cl. ............... 118/629; 118/326; 118/DIG. 7; 132/333; 604/289; 604/290

(58) Field of Classification Search ............... 118/620, 118/629, 326, DIG. 7, 321, 31.5, 634; 427/458; 604/289, 290; 132/333; 4/525; 435/285.2, 435/285.3; 239/690, 704–708

See application file for complete search history.

(56) References Cited

U.S. PATENT DOCUMENTS

| | | | |
|---|---|---|---|
| 1,982,509 A | 11/1934 | Frank | |
| 3,001,980 A | * 9/1961 | Tirtiaux et al. | ............ 525/107 |
| 3,976,031 A | * 8/1976 | Itoh | ............ 118/629 |
| 4,004,733 A | 1/1977 | Law | |
| 4,289,276 A | 9/1981 | Bollina et al. | |
| 4,343,433 A | 8/1982 | Sickles | |
| 4,357,900 A | 11/1982 | Buschor | |
| 4,664,315 A | 5/1987 | Parmentar et al. | |
| 4,688,518 A | 8/1987 | Missier | |
| 4,731,058 A | 3/1988 | Doan | |
| 4,846,525 A | 7/1989 | Manning | |
| 4,941,808 A | 7/1990 | Qureshi et al. | |
| 5,043,839 A | * 8/1991 | Wallace | ............ 361/220 |
| 5,101,679 A | 4/1992 | Smith et al. | |
| 5,268,166 A | 12/1993 | Barnett et al. | |

(Continued)

FOREIGN PATENT DOCUMENTS

EP    0 031 649 A2    7/1981

(Continued)

OTHER PUBLICATIONS

Cooper, S. C. and Law, S. E., "Electrostatic Sprays for Sunless Tanning of the Human Body", Proceedings of the ESA-IEEE Joint Meeting on Electrostatics, Jun. 25, 2003, pp. 1-12, University of Arkansas, Little Rock, Arkansas.

*Primary Examiner*—Yewebdar T. Tadesse
(74) *Attorney, Agent, or Firm*—Gardere Wynne Sewell LLP

(57) ABSTRACT

An apparatus and method for electrostatically coating a body surface with a coating composition. An apparatus of the present invention includes an enclosure, a mount positioned on the enclosure, and an electrostatic nozzle connected to the mount, the electrostatic nozzle adapted for passing the coating composition for deposition on the body surface. The apparatus further includes a floor surface within the enclosure, the floor surface having a resistive electrical connection.

47 Claims, 8 Drawing Sheets

U.S. PATENT DOCUMENTS

Figure 1:
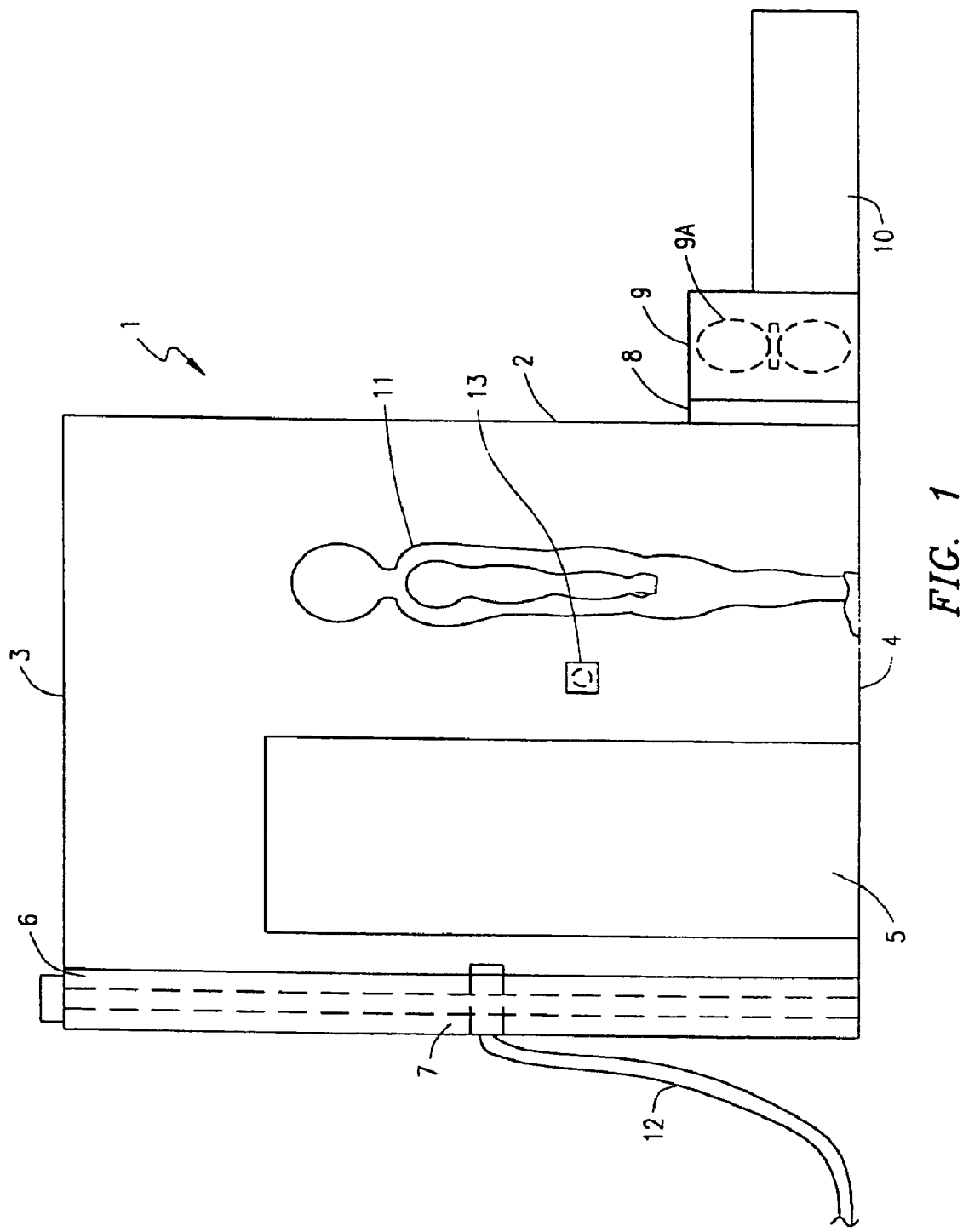

| | | | |
|---|---|---|---|
| 5,277,713 | A | 1/1994 | Gelain et al. |
| 5,322,684 | A | 6/1994 | Barnett et al. |
| 5,387,200 | A | 2/1995 | Kronstadt |
| 5,460,192 | A | 10/1995 | McClain |
| 5,494,674 | A | 2/1996 | Barnett et al. |
| 5,527,564 | A * | 6/1996 | Napadow et al. ............ 427/477 |
| 5,545,140 | A | 8/1996 | Conero et al. |
| 5,664,593 | A | 9/1997 | McClain |
| 5,691,875 | A * | 11/1997 | Dangelmayer et al. ...... 361/222 |
| 5,704,554 | A | 1/1998 | Cooper et al. |
| 5,738,728 | A | 4/1998 | Tisone |
| 5,765,761 | A | 6/1998 | Law et al. |
| 5,833,751 | A | 11/1998 | Tucker |
| 5,863,497 | A | 1/1999 | Dirksing |
| 5,922,333 | A | 7/1999 | Laughlin |
| 6,003,794 | A | 12/1999 | Hartman et al. |
| 6,138,922 | A | 10/2000 | Hartman et al. |
| 6,199,557 | B1 | 3/2001 | Laughlin |
| 6,227,466 | B1 | 5/2001 | Hartman et al. |
| 6,302,122 | B1 | 10/2001 | Parker et al. |
| 6,302,662 | B1 | 10/2001 | Bensley et al. |
| 6,326,062 | B1 | 12/2001 | Noakes et al. |
| 6,387,081 | B1 | 5/2002 | Cooper |
| 6,443,164 | B1 | 9/2002 | Parker et al. |
| 6,554,208 | B1 | 4/2003 | Venuto, Sr. |
| 6,802,830 | B1 | 10/2004 | Waters et al. |
| 2003/0127542 | A1 | 7/2003 | Cooper |
| 2006/0032439 | A1* | 2/2006 | Burato et al. ................ 118/712 |

FOREIGN PATENT DOCUMENTS

| | | |
|---|---|---|
| EP | 0 031 649 B1 | 9/1984 |
| EP | 0 224 352 B1 | 8/1990 |
| EP | 0 441 501 A1 | 8/1991 |
| EP | 0 468 736 A1 | 1/1992 |
| EP | 0 468 736 B1 | 3/1997 |
| EP | 0 441 501 B1 | 8/1997 |

* cited by examiner

MISTING APPARATUS FOR ELECTROSTATIC APPLICATION OF COATING MATERIALS TO BODY SURFACES

CROSS-REFERENCE TO RELATED APPLICATIONS

This application is related to U.S. Pat. No. 6,387,081, incorporated herein by reference.

BACKGROUND OF THE INVENTION

1. Field of the Invention

The present invention relates to a system for uniformly delivering body coating compositions. More particularly, the invention relates to methods and apparatus for applying such coatings onto the body using the principals of charging, transporting and depositing of electrostatically charged spray droplets.

2. Background of the Invention

Conventional body coating products, whether designed for cosmetic, treatment or medical purposes, are often liquid or viscous or semi-solid products. Most of them are produced in the form of lotions or creams. These products are traditionally applied by gentle massage or rubbing-in with the fingers. These methods of application necessitate the addition of relatively large amounts of adjunct material, i.e. other than the one or more active ingredients necessary to achieve the desired result. Most of these adjunct materials are added to create an aesthetically acceptable product and act as a carrier to deliver the active agent to all parts of the skin. These known delivery systems are wasteful of cosmetic raw materials and have limited efficiency in delivering a desired active ingredient to an intended site. Control over the applied dosage is difficult and limited and the application of the product itself is often time consuming and messy.

In addition, the presence of any significant amounts of stabilizing ingredients such as surfactants, polymers, preservatives, etc, may result in the user experiencing stickiness, greasiness, and possibly irritation. This may be particularly pronounced where skin is damaged or diseased, which may make the application of a product by massage or rubbing-in particularly undesirable.

In the case of coating compositions that are typically applied over the entire body i.e. sun tan lotions, self-tanning products, or moisturizers, application by massage or rubbing-in usually requires a second individual. This is necessary because the user of the product cannot reach and evenly coat all parts of the body unassisted. This is a significant disadvantage because a large percentage of the population would not have such an individual available to apply the product to those hard to reach places.

In addition to the above-described systems for delivering skin treatment agents, there are a small number of known examples where a skin cosmetic or therapeutic active is delivered using an aerosol spray. Two such examples are sprays for sunburn and sprains or other sports injuries. However, aerosol sprays, which are well known in the art for delivering personal products, also suffer from several disadvantages. First, the types of product and active agent that lend themselves to effective aerosol spraying are limited. Second, the use of aerosols still results in significant inefficiency and waste through non-target specific application (over-spray). This over-spray results in loss of active material to the atmosphere. It also creates unwanted mists which can damage surrounding objects if the active ingredient is reactive with whatever object the mist happens to fall on. The use of aerosols to deliver skin cosmetic or therapeutic active agents is also believed to be even less efficient than conventional massage or rubbing-in delivery regimes in the context of percentage and evenness of coverage of the skin surface. Although aerosols can be used to reach many of those hard to reach areas of the body that usually require a second individual for full body application, it is still difficult for a user to achieve a good even coating over the entire body without the assistance of another individual.

The skin is, in fact, a very complex material and has many important characteristics which must be considered in the design of an optimized system for delivering cosmetic or therapeutic actives thereto. For example, skin has a multifaceted surface having both lipophilic and lipophobic character. This character allows the skin to "breathe" and release water vapor, yet function as an effective barrier against water, dirt and other unwanted materials. One particularly important physical feature of skin is its very rough surface terrain, which creates a problem in successfully applying a desired skin cosmetic or therapeutic active with complete and even coverage.

In a very different technical field, the principle of electrostatic spraying of liquid and solid materials to increase the effectiveness of applying coating materials to objects is also known. In this technique an electrode of the electrostatic nozzle is raised to a relatively high electrical potential to cause the formulation to be emitted as a spray of electrically charged droplets. These electrically charged droplets seek the closest grounded object. Electrostatic spraying techniques have been proposed principally for only large-scale industrial and agricultural applications. Examples of these applications include delivering reactive materials like paints, adhesives, and other surface coatings, as well as large-scale delivery of pesticides and other agricultural or agrochemical formulations.

More recently, there have been a small number of proposals for utilizing the known principle of electrostatic spraying for delivering particular materials in specific applications other than those mentioned above. For example, EP-A-224352 (Ocular Treatment) suggests the use of an electrostatic sprayer for delivering a pharmaceutically active agent to the eye, to replace conventional ocular treatment using eye drops.

Other proposals for applying the principle of electrostatic delivery to the skin, for example, are disclosed in U.S. Pat. No. 5,268,166 (Cosmetic Application System), U.S. Pat. No. 5,494,674 (Skin Treatment System) and U.S. Pat. No. 5,322,684 (Cosmetic Delivery System). Each of these proposals suggests the same method of electrostatic spray application to coat the skin with different types of chemical compositions. In one proposal (U.S. Pat. No. 5,268,166) the coating compositions are color cosmetics, in another proposal (U.S. Pat. No. 5,494,674) the coating compositions are skin treatment agents, and in the final proposal (U.S. Pat. No. 5,322,684) the coating compositions are cosmetically active agents, such as, perfume.

In all three of the above proposals the basic application method outlined is basically the same:
(a) providing an apparatus which includes:
  (i) a reservoir containing the coating composition to be delivered which is in an electrostatically sprayable form;
  (ii) at least one delivery means which is a nozzle in communication with the reservoir;
  (iii) a high voltage generator generating voltage in the range of 2 to 20 kilovolts powered from an electricity source; and
  (iv) control means for selectively applying the high voltage from the generator to the at least one delivery means; and (b) actuating the said control means to electrostatically spray the coating composition from the at least one delivery means directly onto the skin at an intended site.

The above proposals reference a number of possible "suitable electrostatic spraying hardware" including EP-A-441501 (Electrostatic Spraying Apparatus), EP-A-468736 (Electrostatic Spraying Device and Method), and EP-A-031649 (Containers and Holders Therefor for Use in Electrostatic Spraying). Each of these referenced electrostatic spraying devices are handheld, self contained units where the reservoir, nozzle, generator, and control for applying high voltage from the generator are in the self-contained apparatus. It is apparent from the descriptions of the "suitable electrostatic spraying hardware" that the anticipated use of the methods described in U.S. Pat. Nos. 5,268,166, 5,494,674 and 5,322,684 was to apply the specified coating compositions to the skin on various small, localized areas of the body (e.g., the face) by electrostatically spraying them through a handheld self-contained device.

Although this method of application offers some advantages over aerosol spraying because it would eliminate some of the over-spray problem, it is still difficult to obtain effective uniform coating over the entire body or a substantial portion of the entire body. The uniformity of the coating is impacted by the distance of the nozzle from the skin, the rate of movement of the spray over various parts of the body, the number and intensity of spray bursts necessary to cover the coating area, etc. Because every user will apply the spray differently, each of the variables will vary from user to user and from spray session to spray session. Consequently, the lack of consistency in performance will affect the consumer's acceptance of this product concept.

In another technical field, spray painting, booths have been used to contain spray mists created by air or electrostatic spray painting of objects. These booths prevent the over-spray from landing on surrounding objects that were not part of the desired target. As the art of spray painting booth has evolved one undesirable result, particularly in the case of electrostatic powder painting, has been the coating of the walls of the spray booth which requires labor and down time to clean off. This coating of the booth walls is particularly costly in electrostatic powder coating because the powder adhering to the walls cannot be effectively recycled and the cost of materials is increased.

There have been a number of proposals to resolve this problem of the booth walls being coated. U.S. Pat. No. 5,833,751 (Powder Coating Booth Having Smooth Internal Surfaces) proposes, "a powder coating booth comprising a pair of identical polycarbonate shells disposed opposite each other to define a coating chamber having smooth, curvilinear surfaces to facilitate the recovery and recycle of excess coating powder."

U.S. Pat. No. 5,277,713 (Cabin for Spray Coating Objects with Powder), for example, describes a cabin for spray coating objects with powder. In the Summary of the Invention it is specified "[w]ith the present invention, the advantages obtained are that the cabin can be produced in a very inexpensive manner, and nevertheless offers greater reliability against electrical arcing, and is electrostatically neutral, or has a repelling effect for many different kinds of powders, so that no or only a few powder particles can collect on the inner surfaces of the cabin." Moreover, U.S. Pat. No. 5,527,564 (Method and Apparatus for Repelling Overspray in Spray Paint Booths) describes a method and apparatus for repelling over-spray in spray paint booths. In the Summary of the Invention of the '564 patent, it is specified, "[a]mong its several aspects and features, the present invention provides an electrically charged panel which repels electrically charged dry or wet coating particles inside an electrostatic spray painting booth, or other booths having charged paint or powder particles therein." Later in the Detailed Description of the Preferred Embodiment of the '564 patent it is noted, "Better painting efficiency is achieved because the repelled paint particles will become available to adhere to the articles being painted".

Until recently, however, prior art in electrostatic spraying technology required that high voltage, 5 to 80 kilovolts, be generated and that the electrostatically sprayable compositions have relatively high resistivity, in the range of 100,000 to 100,000,000,000 ohm centimeters. High voltage types of electrostatic nozzles make aqueous solutions very difficult to spray effectively using electrostatic means due to the highly conductive nature of water-based sprays. Because of the resistivity limitations it was recommended that the compositions be non-aqueous or contain very small amounts of water, e.g., on the order of less than 5%. The non-aqueous solution requirement meant that the most effective and inexpensive carrier for the active coating ingredients could not be used effectively with this process. In addition, the high voltage requirements made electrostatic spraying of coating materials on the human body too dangerous to be seriously considered.

However, recently there have been innovations in the field of electrostatic spray nozzles that have made this process more acceptable for the application of coating compositions in various fields such as industrial and agricultural applications. For example, U.S. Pat. No. 5,765,761 (Electrostatic-Induction Spray-Charging Nozzle System) and U.S. Pat. No. 5,704,554 (Electrostatic Spray Nozzles for Abrasive and Conductive Liquids in Harsh Environments) describe "air atomizing induction charging spray nozzles suitable for use with conductive liquids, solutions, suspensions or emulsions". The major advantage of the described method is the high level of spray charging that can be achieved at very low electrode voltages and power. The total power required is very low, typically less than 0.5 watts per nozzle with very conductive water-based spray liquids. The introduction of this new air-assisted induction charging system (AAIC), which operates with low voltage and low current, makes it possible to utilize electrostatic spraying to create an electrostatic mist that could be used to apply a coating composition to the human body without any risk of electrical hazard to humans.

The typical approach to developing conventional uncharged automated spray tanning systems has been to mount many nozzles at various heights or angles around the subject in an effort to apply an even coating. Typically, the customer is instructed to move through a variety of poses during the spray event which usually lasts less than 30 seconds. With these conventional spray methods there are often less than optimum tanning results due to missed or thinly coated areas, and dark runs and streaks occur from over application. Presently used tanning compounds are expensive and the poor spray deposition efficiency reduces the profit margins of the spray tanning system. Less than optimal mass transfer of the tanning compound results in a light tanning color that fades more quickly than a heavier initial application. In addition, even though the tanning compounds are safe materials, the level of respirable aerosols can be high during and after the spray process and may be irritating to some customers. If ventilation is poor, lingering aerosols can be carried throughout the salon and create high levels of unwanted dust deposits on store fixtures.

U.S. Pat. No. 6,387,081 (Misting Apparatus For Application Of Coating Materials To Skin Surface) describes an apparatus and method for electrostatically coating a human with a coating composition. An embodiment of U.S. Pat. No. 6,387,081 includes an enclosure; a mount positioned on the enclosure; an electrostatic nozzle connected to the mount, the electrostatic nozzle for passing the coating composition; and a grounding connection positioned inside the enclosure, the grounding connection capable of directly electrically grounding the human, wherein the coating composition is depositable upon the human. This prior art electrostatic spray system provides a conductive plate, with a wire directly connected to ground. A human subject stands on this plate during the spray process. The plate serves to electrically earth the human spray target with a negligible resistance from plate to earth (i.e. less than 1 ohm). The presence of the directly-grounded metal plate contacting the feet and adjacent to the sides of the feet can cause preferential deposition on the feet and ankles due to the increased electric field strength in these areas. In addition, whole-body spray uniformity may be affected due to the head-to-toe potential gradient that forms during charge transfer of spray over the resistive skin surface of a human target standing on a directly grounded metal plate. An electrically resistive floor would serve to slow charge decay time, slightly elevating the electrical potential of the target and reducing the electrical potential difference between upper and lower body portions. If the resistance between the feet and earth is significantly greater than the overall human body resistance, electrical potential would be beneficially equalized from head to toe. Human body skin surface resistance from head to toe is normally in the range of 200 k ohms. Therefore, a resistive ground of greater than 10 times the target body resistance (i.e. 2 megaohms) would be sufficient to equalize potential differences from head to toe.

In addition, it would be desirable to maintain resistance of the human subject to earth in the range of $10^5$ and $10^9$ ohms for safety. This resistance range is sufficient to allow adequate charge transfer for electrostatic spray deposition without significant charge accumulation, yet will provide protection in the case of accidental contact with electrical mains. (JA Cross—Electrostatic Principles, Problems and Applications, Adam Hilger Publishing Bristol, England 500 pages, 1987, ISBN 0-85274-589-3). However, it should be noted that commercial versions of U.S. Pat. No. 6,387,081 operate on reduced voltage, and this design prevents the chance of human contact with the mains voltage while the human subject is standing on the grounding plate.

Although satisfactory results have been obtained using the invention of U.S. Pat. No. 6,387,081, in accordance with the present invention it has been determined that very satisfactory results can be obtained without directly grounding the human spray target. The present invention provides for a method and apparatus for electrostatically coating a human with a coating composition which provides for improved mass transfer and uniformity of spray solution onto the body. An additional advantage of the present invention is that it provides for a reduction in the level of respirable aerosols present in the spray environment.

BRIEF SUMMARY OF THE INVENTION

As an improvement upon existing systems and methods, the present invention provides an apparatus and method for electrostatically coating a body surface with a coating composition. One embodiment of the present invention is directed to an apparatus for electrostatically coating a body surface with a coating composition, the apparatus including an enclosure, a mount positioned on the enclosure, and an electrostatic nozzle connected to the mount, the electrostatic nozzle adapted for passing the coating composition for depositing upon the body surface. The apparatus further includes a floor surface, not directly grounded by a wire, within the enclosure, the floor surface adapted to provide adequate charge leakage paths to discharge spray deposited onto the body surface.

Another embodiment of the present invention is directed to a method for applying a coating composition to a body surface. The method includes the steps of misting at least a portion of an electrostatically charged coating solution on a body surface and depositing the at least a portion of the electrostatically charged coating solution on the human by electrostatic space-charge and image-charge forces. The electrically charged droplets seek targets of different electrical potential and discharge upon contact. According to the present invention, in the case of negatively charged spray, the desired body surface target can be earthed through a resistive pathway, or it may be raised to a positive potential, or it may be at a negative potential that is significantly less than that of the electrically charged spray cloud. Conversely, in the case of positively charged spray, the desired target may be earthed through a resistive pathway, or it may be raised to a negative potential, or it may be at a positive potential that is significantly less than the equivalent potential of the charged spray cloud.

BRIEF DESCRIPTION OF THE DRAWINGS

A more complete understanding of the method and apparatus of the present invention may be obtained by reference to the following Detailed Description when taken in conjunction with the accompanying Drawings wherein:

FIG. 1 is a schematic view of one embodiment of the booth;

FIG. 2 is a schematic view of the operation of the booth of FIG. 1;

FIG. 3 is an expanded view of the electrostatic principles at work during operation.

FIG. 4 is a drawing of the application system;

FIG. 5 is a view of an alternate embodiment of a booth constructed in accordance with the principles of the present invention;

FIG. 6 illustrates an embodiment of an electrostatic spray chamber used for obtaining the experimental results of the present invention;

FIG. 7 illustrates a plot of the transient potential measured on a human subject during a charged spray treatment in accordance with the principles of the present invention; and FIG. 8 illustrates a ratio of uncharged to charged respirable aerosols measured during and after spray sessions.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be constructed as limited to the embodiments set forth herein; rather, these embodiments are provided so that this disclosure will be thorough and complete, and will fully convey the scope of the invention to those skilled in the art.

Although the present invention is open to various modifications and alternative constructions, a preferred exemplary embodiment that is shown in the drawings is described herein in detail. It is to be understood, however, that there is no intention to limit the invention to the particular forms disclosed. One skilled in the art can recognize that there are numerous modifications, equivalences and alternative constructions that fall within the spirit and scope of the invention as expressed in the claims.

An embodiment of the present invention is illustrated in FIG. 1. The booth 1 consists of walls 2 which can be constructed of a dielectric (non-conducting) material (preferably a thermoplastic which can be thermoformed in to the desired shape), a ceiling 3 that can be constructed of the same dielectric material, and a door 5 that can be constructed of the same dielectric materials as the walls and ceiling. In one embodiment of the present invention, the booth 1 is constructed of flat dielectric panels of high density polyethylene joined together by aluminum extrusions. The booth 1 is further comprised of a floor surface 4 which does not have a direct connection to a ground. The floor surface 4 is adapted to provide adequate charge leakage paths to ground or may be at an elevated voltage during a spraying operation, thus providing an indirect connection to ground. In one embodiment of the present invention, the floor surface 4 is comprised of a floor having a dielectric coating. In another embodiment of the present invention the floor surface 4 can be constructed of a PVC plastic encapsulated steel mesh floor over a fiberglass sump base.

Attached to one end of the booth 1, is a motion apparatus 6, which can be used to provide vertical (and in one embodiment horizontal) motion to at least one electrostatic nozzle 7 that is mounted to the motion apparatus 6. In one embodiment, the electrostatic nozzle 7 is rotated/pivoted in an up-and-down direction rather than moved in a vertical direction. Attached to the base of the wall 2 opposite the motion apparatus 6 is an exhaust housing 9 that can be opened on the end attached to the wall 2 and connected to an exhaust conduit 10. The exhaust housing 9 can be made of a dielectric material and can contain an exhaust filter 8 on the open end attached to the wall 2 and an exhaust pen 9A.

When the booth 1 is in operation, a user 11 stands inside the booth 1 in contact with the floor surface 4. The floor surface 4, which does not have a direct connection to ground, is adapted to provide adequate charge leakage paths from the user 11 to ground during the spraying operation. In an alternative embodiment of the present invention, the user 11 can stand upon a plate having no direct connection to ground placed upon the floor 4, such as a plate made of and/or coated by a dielectric material or a semi-conductive material. Although the preferred embodiment is described as using a floor having no directed connection to ground, it should be understood that other methods for providing a surface in which no direct connection between the surface and ground is required can be used. For example, in another embodiment of the present invention, a metal plate which is not directly grounded by a wire can be used. In still another embodiment of the present invention, the floor 4 may be comprised of a metal floor having no direct connection with ground. In all of these embodiments the indirect ground may be a resistive connection to ground or may be a connection to a positive or negative voltage source.

Figure 2:
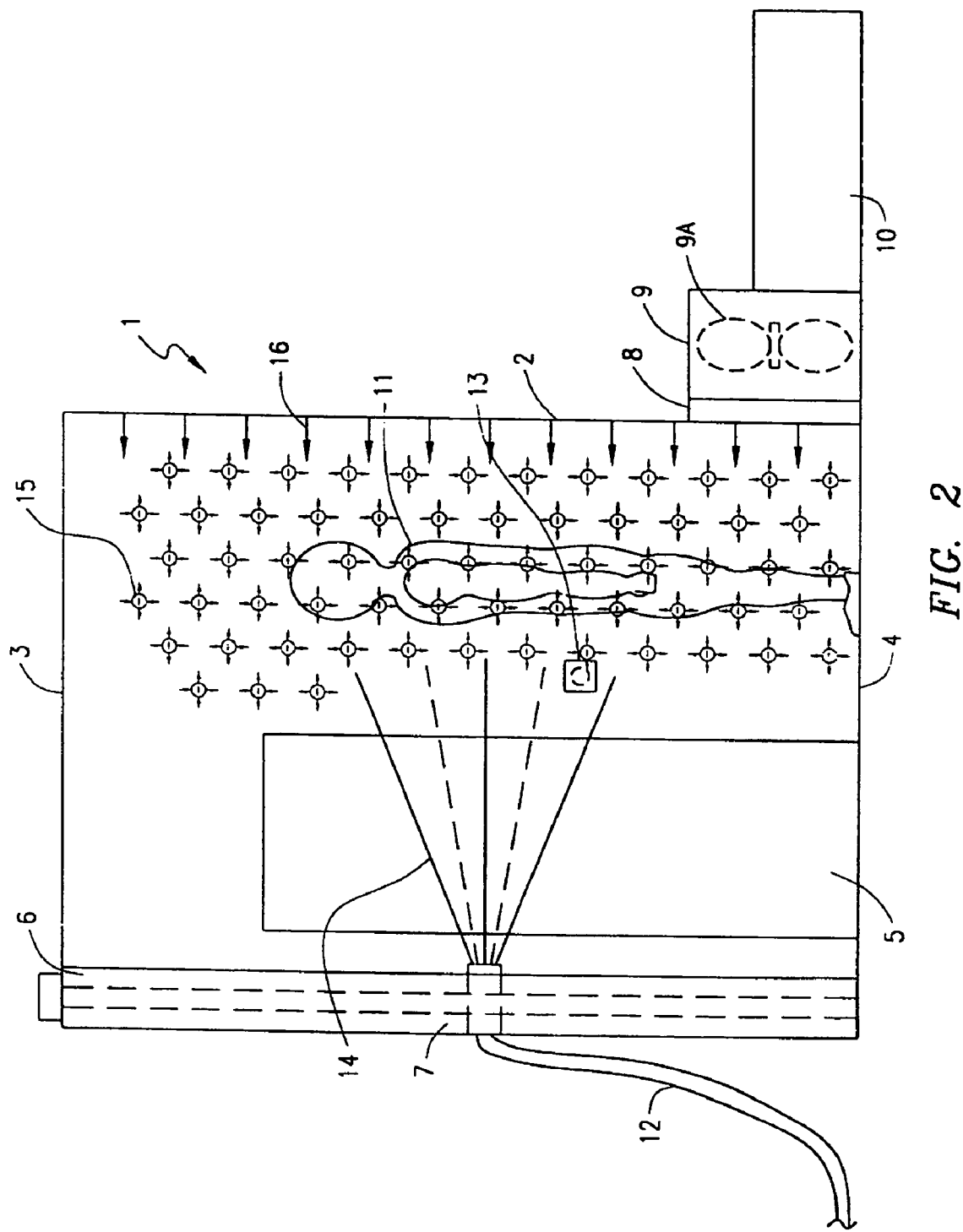
Figure 4:
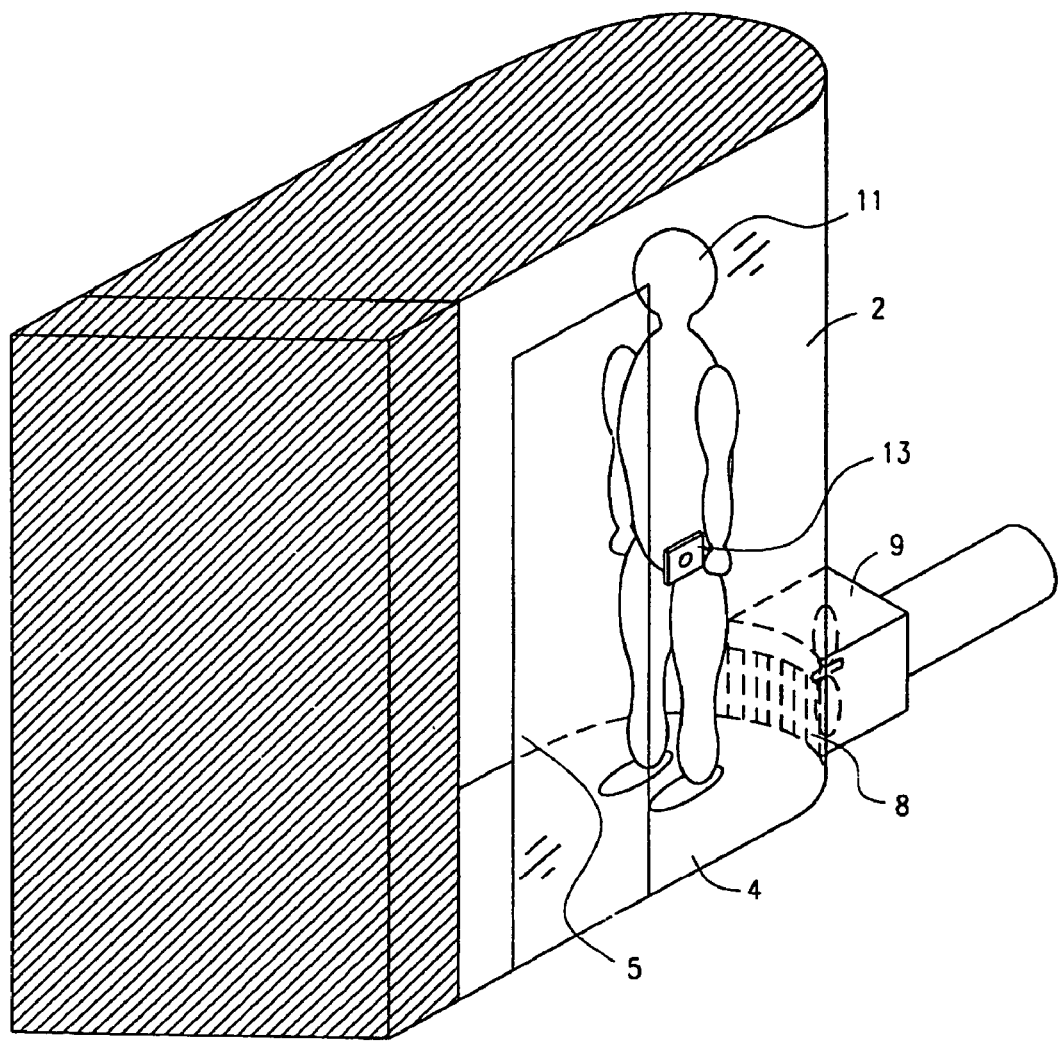

Referring now to FIG. 2, there is illustrated the electrostatic misting booth 1 in operation. When the user 11 enters the booth 1, he closes the door 5 and stands at a predetermined spot upon the floor surface 4 having no direct connection to ground, which can be at an elliptical end of the booth, as shown in FIG. 4, facing the electrostatic misting nozzle(s) 7. He could activate the system by pressing the start button 13 or by any other means. This activates a misting cycle from the electrostatic misting apparatus 12 that can be configured to deliver a specific volume of the coating composition. One example of a coating composition that might be used is a sunless tanning solution made of water (70%), dihydroxyacetone (8.75%), bronzing dye (7%), Carbopol 940 solution (4.2%), Propylene Glycol (1%), Lexorez TC-8 (3%), Octyl Palmitate (2%), and the following components in concentrations of less than 1%; Methyl Paraben, Germall II, Aloe Vera 10X, L-Tyrosine, Stearic Acid, Stearyl Alcohol, Glyceryl Monosyearate SE, Isopropyl Myristate, and Triethanolamine.

As the coating composition passes through the nozzle(s) 7 the composition is atomized into tiny droplets 15 and the droplets are charged. Because particles of like charges repel each other, once they leave the nozzle(s) 7, the droplets 15 spread into a mist. As the misting process is occurring, the nozzle(s) 7 can be moved (vertically, horizontally, or rotated) by the motion apparatus 6 to more evenly distribute the mist. Once the charged droplets 15 enter the larger space in the booth 1 they separate from each other rapidly and begin to fill the booth 1 with an electrostatic mist.

The user 11 would be standing downstream of the airflow 14, and the initial force of the airflow 14 and/or the electrostatic force between the user 11 and the charged droplets 15 can result in the creation of a uniform layer of the coating composition on the front side of the user 11. As the charged particles 15 move past the user 11 they lose the horizontal momentum generated by the airflow 14 of the nozzle(s) 7, and begin to succumb to the forces of gravity and descend vertically. As these excess charged droplets descend they are attracted to neutral objects, or objects of an opposite potential, or objects of the same polarity but with less electrical potential than the spray cloud. Because the walls 2 are the first neutral object these excess droplets 15 come into contact with they can quickly begin to attach to the walls 2. Due to the dielectric nature of the walls 2 the negative charges passed on by the charged droplets 15 soon create a negative electrostatic charge 16 on the walls 2. Once this occurs the electrostatic charge 16 on the walls 2 begins to repel the remaining charged droplets that are descending. In an alternative embodiment, the walls 2 can be charged or coated with a charged material, such as an inert charged water spray or air ions, prior to the excess droplets 15 coming near them. In this way, the walls 2 then can repel the excess droplets even more efficiently.

In the beginning of the spraying operation, the user 11 possesses a substantially neutral charge. Initial contact of the charged droplets with the user 11 results in a small accumulation of charge upon the body of the user 11, and the electric potential of the skin surface of the "electrically floating" human target equalizes. Very quickly after the beginning of the spraying process, the increasing humidity of the environment of the booth 1, as well as the introduction of the water based spray on and around the user 11, causes the formation of ground-current leakage paths. These ground-current leakage paths allow the transfer of charge from the user 11 to a ground in order to dissipate the accumulated charge resulting from the deposition of the charged droplets upon the user 11. In accordance with an embodiment of the present invention, the resistance from the user 11 to ground of the current leakage paths is less than 5000 Megaohms. As a result, the development of significant voltage potentials and potential differences from head to toe on the body of the user 11 is limited.

Figure 3:
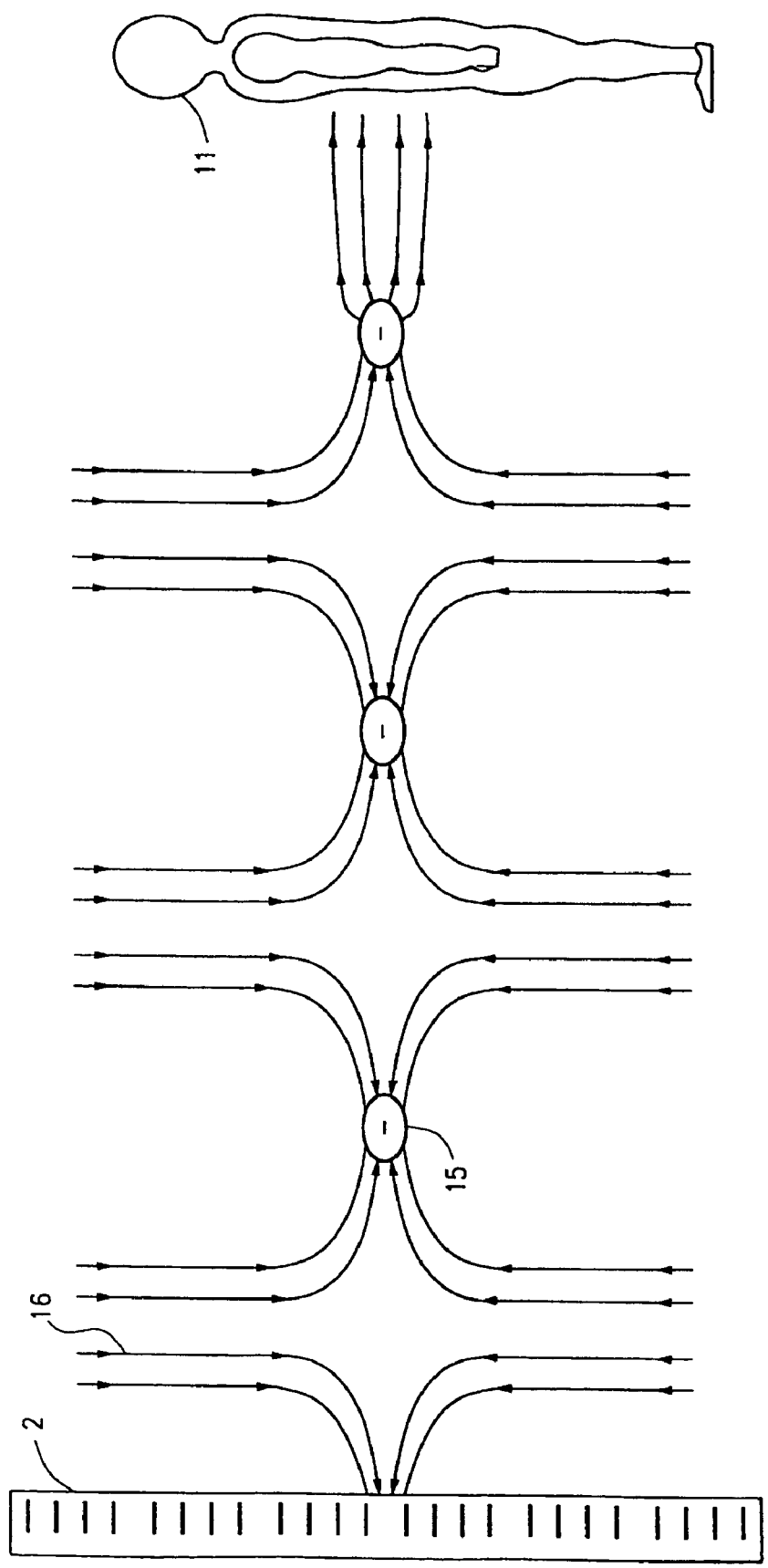

Now referring to FIG. 3, there is illustrated the electrostatic coating process resulting in the booth 1. Because electrostatic forces 16 are exerted perpendicular to the charged surface, the electrostatic charge on the walls 2 repels the charged droplets toward the center of the booth 1. Because the booth 1 is filled with a mist of charged droplets 15 each charged droplet 15 that is repelled from the walls exerts an electrostatic force on the charged droplet 15 next to it, thus forcing that charged droplet 15 towards the center of the booth. This process is repeated until a charged droplet 15 is close enough to the user 11 at the center of the booth 1 to be attracted to him/her. Once this occurs the electrostatic forces 16 deposit the charged droplet onto the skin of the user and forms a thin coating. This process is continuous as the charged droplets descend downward. The result is an even layer of the coating composition over the user 11. Because the quantity of coating material on the front of the user 11 might be more than that on the backside due to the additional deposition caused by the airflow 7, the user could turn around and repeat the procedure to have an even coating over the whole body. Although, in one embodiment, the user need not turn to achieve an even coating.

Referring back to FIG. 2, once the second coating process is complete an exhaust fan 9A starts and pulls the excess mist through a filter 8 into an exhaust conduit 10 to remove the remaining residual charged droplets 15 from the booth 1.

Referring now to FIG. 4, there is illustrated a view of one embodiment of the misting system at rest. This drawing illustrates that in a preferred embodiment the booth 1 walls 2 would create an elliptical shape on one end that can approximate the horizontal shape of the human body and, therefore, could be an ideal configuration for maintaining the walls 2 equidistant from the user 11. As discussed in regard to FIGS. 1-3, the booth 1 is further comprised of a floor surface 4 having no direct connection to ground, and adapted to provide adequate charge leakage paths to ground during a spraying operation. When the booth 1 is in operation, the user 11 stands inside the booth 1 in contact with the floor surface 4. In an alternative embodiment of the present invention, the user 11 can stand upon a plate placed upon the floor surface 4, such as a plate made of and/or coated by a dielectric material, such that the user 11 has no direct connection to ground, or has a resistive connection to ground. Although the preferred embodiment is described as using a floor having no direct connection to ground, it should be understood that other methods for providing a surface in which no direct connection between the surface and ground is required can be used. For example, in another embodiment of the present invention, a metal plate which is not directly grounded by a wire, or a plate, or floor surface with a resistive wire can be used. In still another embodiment of the present invention, the floor 4 may be comprised of a metal floor having a resistive connection with ground. Alternatively, the floor surface or plate could be connected to a voltage source to elevate the potential of the sprayed subject, either the same or opposite polarity of the spray, depending on the electrostatic effect desired.

Figure 5:
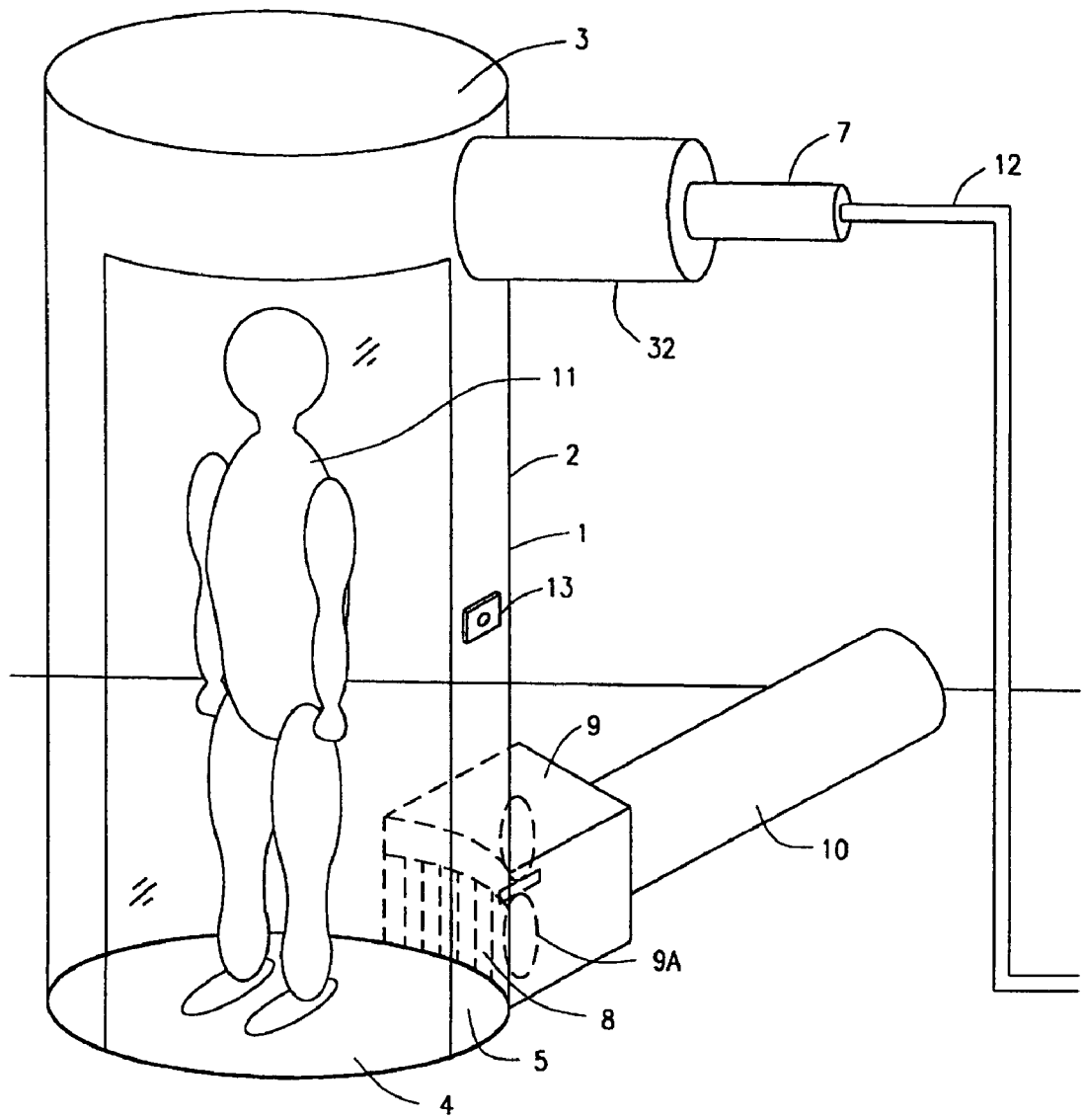

In another embodiment of the present invention, the misting solution is disbursed through the use of a misting chamber rather than moving nozzles. For example, FIG. 5 illustrates a booth 1 using a misting chamber 32. The booth 1 consists of walls 2, a ceiling 3 and door 5, all of which can be made of dielectric material. The booth 1 also includes a floor 4 floor surface 4 which does not have a direct connection to a ground. The floor surface 4 is adapted to provide adequate charge leakage paths to ground during a spraying operation. In one embodiment of the present invention, the floor surface 4 is comprised of a floor having a dielectric coating. In another embodiment of the present invention the floor surface 4 can be constructed of a PVC plastic encapsulated steel mesh floor over a sump base.

Attached to the upper section of one of the walls 2 or to the ceiling 3, high enough to be above the head of any person who may use the booth, is a misting chamber 32 which consists of a cylinder made of a dielectric material open on the end attached to the wall 2 or ceiling 3 enclosed on the end away from the wall 2 or ceiling 3. Attached to the closed end of the misting chamber 32 is at least one electrostatic nozzle 7 which is part of the electrostatic misting apparatus 12 used to create the electrostatic mist. Attached to the base of wall 2 is an exhaust housing 9 which is opened on the end attached to the wall 2 and connected to an exhaust conduit on the end away from the wall 2. The exhaust housing 9 is made of a dielectric material and contains an exhaust filter 8 on the open end attached to wall 2 and exhaust bin 9A. When the booth 1 is in operation, the user 11 stands inside the booth 1 in contact with the floor surface 4. The floor surface 4, which does not which does not have a direct connection to ground, is adapted to provide adequate charge leakage paths from the user 11 to ground during the spraying operation. Alternatively, the floor surface could be connected to a voltage source to elevate the potential of the sprayed subject, to either the same or opposite polarity of the spray, depending on the electrostatic effect desired. In an alternative embodiment of the present invention, the user 11 can stand upon a plate having no direct connection to ground placed upon the floor 4, such as a plate made of and/or coated by a dielectric material or a semiconductive material. Although the preferred embodiment is described as using a floor having no directed connection to ground, it should be understood that other methods for providing a surface in which no direct connection between the surface and ground is required can be used. For example, in another embodiment of the present invention, a metal plate which is not directly grounded by a wire can be used. In still another embodiment of the present invention, the floor 4 may be comprised of a metal floor having no direct connection with ground.

In another embodiment of the present invention, a device is included that produces a negative electrostatic charge on the walls 2 of the booth. By producing a negative electrostatic charge on the walls of the booth, the charged particles of the misting solution are repelled from the walls 2 with greater force, thereby increasing the efficiency of moving the charged droplets to the center of the booth. The desirable charge on dielectric wall surfaces may be formed in a number of ways. The simplest method is to allow charged spray droplets to impinge on the walls. This charges the walls to the same polarity as the spray and, when the charge causes the wall potential to reach near the equivalent potential as the spray cloud, the incoming droplets reverse direction away from the wall and toward the human target of lower potential. Another method to charge the walls is by dispensing air ions (of the same polarity as the spray) in the chamber which pre-charge the dielectric surfaces and repel the charged spray droplets. Another advantage to dispensing air ions may be to increase the space charge within the chamber. Additionally, mechanical means may be used to prevent wall coating. For example, a perforated inner wall layer (not illustrated) can be added to the misting booth and air can be forced outward through the perforations toward the center of the booth, thereby forcing the charged droplets away from the wall and toward the center of the booth. Furthermore, the booth shape can be altered to include circular, hexagonal, octagonal, or even rectangular shapes, and one embodiment of the present invention includes misting nozzles at different sides of the booth, possibly, with the user positioned between them. By positioning the misting nozzles in this fashion, the user can be coated in his entirety without rotating. Alternatively, the misting nozzles can be spaced throughout the booth to provide even coating.

Formulations for sunless tanning applied in spray form typically are conductive, aqueous-based solutions of resistivity below $10^4$ ohm-cm and are typically delivered at a rate of 100 to 200 ml per tanning session. To adequately charge the electrically conductive solution an air-atomizing induction-charging type nozzle was chosen for use in obtaining the experimental results of the present invention. An example of an air-atomizing induction charging nozzle that may be used is one of the embodiments of the spray nozzles described in U.S. Pat. No. 5,704,554, incorporated herein by reference. This induction-charging nozzle has the advantage of low voltage (0.5 to 1.5 kV) and low operating current (0.2 to 0.5 mA at 1 kV) from the nozzle's power supply and is capable of imparting adequate charge-to-mass levels of −10 to −15 mC/kg.

Figure 6:
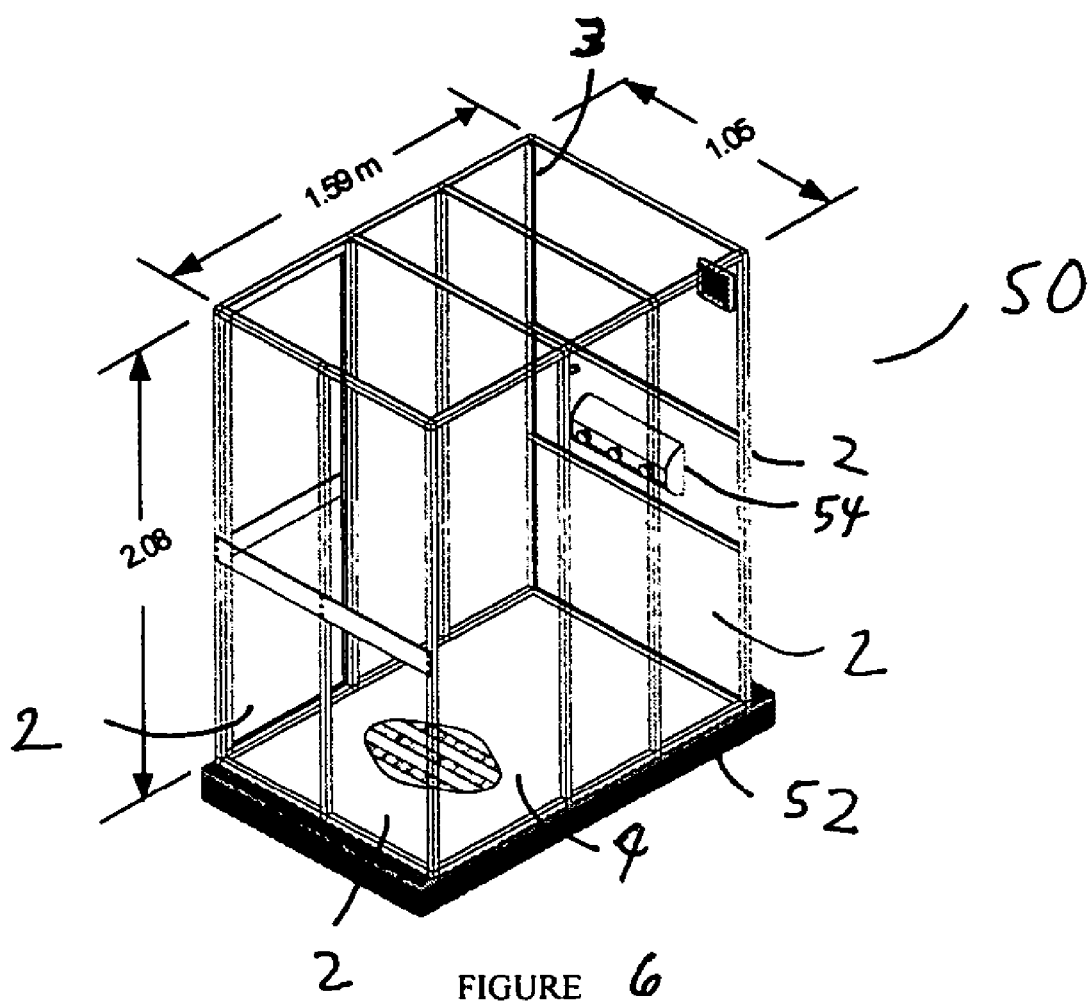

FIG. 6 illustrates an embodiment of an electrostatic spray chamber used for obtaining the experimental results of the present invention. The electrostatic spray chamber 50 is constructed of flat dielectric panels, for example of high density polyethylene, joined by aluminum extrusions forming walls 2 and a ceiling 3. The electrostatic spray chamber is further constructed of PVC plastic encapsulated steel mesh floor 4 over a fiberglass sump base 52.

The electrostatic spray chamber further includes three charging nozzles that are arranged on an oscillating drum 54 on one end of the electrostatic spray chamber as shown in FIG. 6. The 75 degree movement of the nozzle drum, which continuously oscillated during the spray treatments, caused the spray to sweep over the target subject from head to foot at 1.13 rad/s. The spray system's programmable controller was set to spray for a 14 second period on the subject's front side, pause to allow the subject to turn 180°, then apply a 14 second spray to the subject's backside. Each side received 10 full spray passes during the spray treatments. Each of the three nozzles was set to deliver a liquid volume of 1.2 ml/s for a total of 100 ml dispensed during the 28 second spray event.

The necessity for directly grounding the subject was evaluated by measuring capacitance, leakage resistance and voltage of both human and mannequin target subjects with the grounded floor plate removed. It was theorized that in the humid environment of the spray chamber, with conductive spray being applied, there would be sufficient ground-current leakage paths established to provide a resistive indirect ground that would prevent significant charge from accumulating on the subject. In the presence of such significant charge leakage paths, the target potential will have a value of $V=I_dR$, where $I_d$ is the deposition current due to charged spray impacting the target and R is the resistance of the leakage pathways to earth over contaminated dielectric surfaces. Without such leakage paths the target potential would be elevated to $V=q/C$, where q is charge from spray delivered to the sprayed target and C is target capacitance. Capacitance values for human subjects have been reported in the range of 125-250 pf (See McAteer, O. J., Electrostatic Discharge Control, McGraw-Hill Publishing Company, New York, N.Y., 480 pages, 1990, ISBN 0-07-044838-8). With these relatively small capacitance values, target potentials due to charge accumulation can be significant in the absence of adequate leakage pathways.

During the indirectly grounded subject tests, the grounding plate was removed and the subject was positioned directly on the vinyl coated steel mesh floor. The subject was separated from the conductive mesh by a 3 mm thick dielectric coating which completely encapsulates the steel mesh. The encapsulated steel mesh did not have a direct electrical connection to ground and rested on top of the fiberglass base which held it 10 cm above a concrete floor. Capacitance was measured by touching several surface locations of the subjects with the probe of a capacitance meter, for example, a B&K Precision Model 890 capacitance meter. Resistance was measured with an electrometer, for example, a Keithley Model 610B electrometer. These electrical measurements were made first in a dry and clean spray chamber. Subsequent measurements were made after the spray sessions to detect changes due to dielectric surface contamination by the conductive spray liquid. During the charged spray treatments, using tap water onto the indirectly-grounded subjects, the transient voltage of the subject was observed. This was done for both mannequin and human target subjects. Transient voltage measurements were made with a voltage probe connected to a digital multimeter, for example, a Keithley 40 kV, 1000:1 voltage divider probe connected to a Radio Shack Model 22-812 digital multimeter having an RS-232 computer interface. The voltage probe was connected to the head of the mannequin target, and held in the hand during spray treatments onto the human subject. It was verified early in the experiment that the voltage measurement observed on the subject during spraying did not vary significantly with respect to probe location on the body. The upper-body potentials observed were very similar to those observed at lower body sample locations.

In a cleaned and dry chamber, prior to a spray session, the electrical resistance from subject to ground (without a direct-ground plate) was measured in the $80 \times 10^9$ Ω range for the mannequin target and $60 \times 10^9$ Ω for the human target. The difference was most likely due to a wooden stand employed to hold the mannequin upright. The measured capacitance values were 250 pF for the mannequin and 265 pF for the human. These values are in the range previously published for a human subject in shoes with a 1 cm sole having a dielectric constant of 5. After a 14 second spray period, the values of resistance were greatly reduced to an average of $25 \times 10^6$ Ω. Based on this reduced leakage resistance and assuming a −40 µA total spray current from the three nozzles intercepted by the target, the calculated target potential should only reach −1 kV. Such a potential level is very negligible compared to the equivalent potential produced by the spray cloud's space charge.

Figure 7:
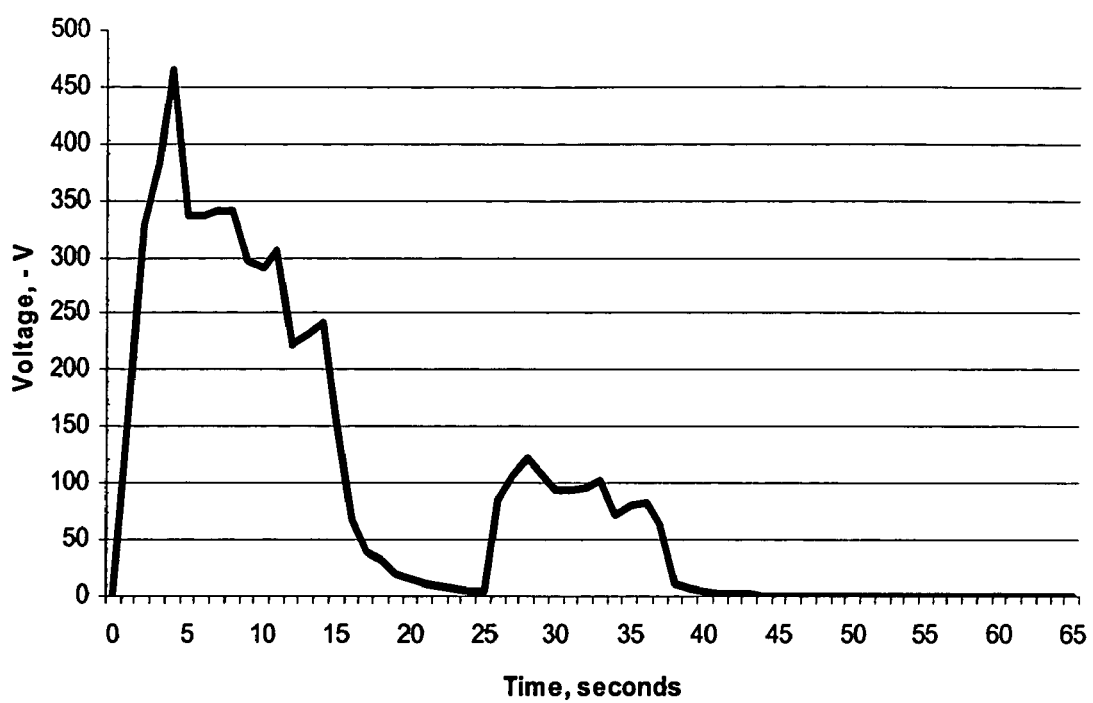

The transient voltage on the subject during a charged spray treatment was measured for both mannequin and human targets. For these trials, the spray system was set to deliver a 14 second spray, followed by a 10 second rest, followed by another 14 second spray. Each spray trial was begun with a cleaned and dried booth. A plot of the transient potential measured on a human subject during the spray event is illustrated in FIG. 7. These are typical results and were similar for mannequin and human subjects. The maximum level of transient potential obtained attained was only approximately −450V. This level was less than theoretically calculated and can be attributed to current leakage paths forming very quickly during the spray process. As illustrated in FIG. 7, at the beginning of the first spray cycle the target voltage increased almost immediately to the maximum level. Then, while charged spray was continuing to impact the target, the voltage decreased rather than increased. It is likely that leakage resistance was being reduced as more water-based spray was being introduced on and around the subject. At the beginning of the 10 second rest interval the charge dissipated very quickly. At 24 seconds, when the spray began again for another 14 second cycle, the peak voltage was only about ¼ the peak level seen during the initial cycle. As illustrated by the transient voltage graph of FIG. 7 the voltage measured on the indirectly-grounded human subject during charged spray treatments indicates that resistive current leakage paths are sufficient to prevent significant charge accumulation on the subject.

During the spray trials it was visually observed that much greater quantities of lingering mist were present after the uncharged spray treatments. Much less airborne mist was noticed after charged spray treatments. Therefore, a study of mist concentrations during charged and uncharged spray sessions was conducted in the presence subjects who were not directly grounded. Continuous air sampling was conducted using a TSI DustTrak Model 8520 Aerosol Monitor with an attached 10-mm Nylon Dorr-Oliver Cyclone to discriminate between the human-respirable fraction and larger-sized aerosol particulates. The intake to the aerosol monitor was positioned near the nose and mouth of the subject mannequin target which remained in the booth during the charged and uncharged spray sessions while air sampling was conducted.

Measurement of respirable airborne mist concentrations during and after charged and uncharged spray treatments were performed. An air sampler, fitted with a cyclone separator that mimics human respiratory response, indicated peak respirable droplet concentrations of 45 mg/m$^3$ during charged spray treatments. The uncharged spray exhibited peak values well over the maximum 150 mg/m$^3$ range of the instrumentation. To put these numbers in perspective, 5 to 38 mg/m$^3$ of respirable mist was measured during a hot shower. A peak value of 14 mg/m$^3$ was measured after a 5 second spray of household air freshener in a small room.

Figure 8:
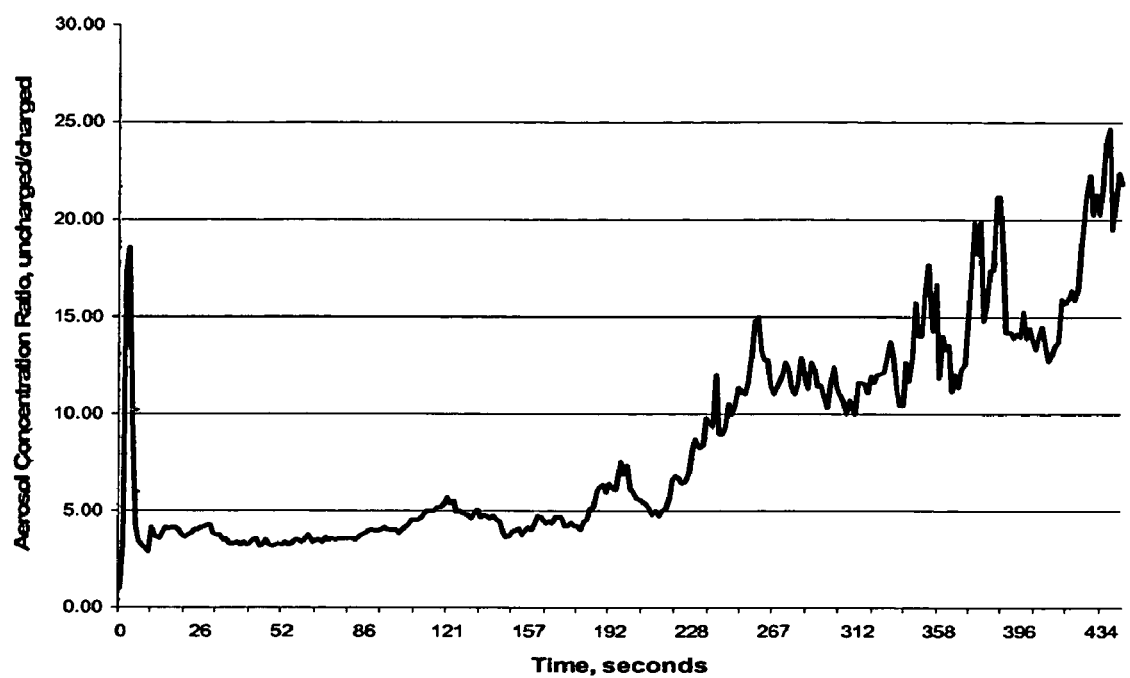

FIG. 8 illustrates the ratio of uncharged to charged respirable aerosols measured by a cyclone sampler during and after spray sessions. FIG. 8 illustrates the ratio of uncharged to charged spray mist in the respirable droplet diameter range drawn into the air sampler during a 38 second spray session and for 6 minutes afterward. During the spray session the air-sampler measured nearly five times more respirable aerosols during an uncharged spray treatment than during a charged spray treatment. This is probably due, for the most part, to efficient electrostatic deposition of the spray onto the target during charged spray sessions. However the charged spray may have reduced the ability of the tiny droplets to enter into the small sampler orifice due to Faraday cage effects. After the spray session, both charged and uncharged aerosol concentrations were rapidly reduced. However, FIG. 8 illustrates that the amount of droplets drawn into the sampler during uncharged spray was over ten times that of charged spray 3.5 minutes after the spray session ceased.

The experimental results of the present invention have shown that direct grounding of the subject was not necessary to prevent excessive charge buildup that would reduce the electro-deposition benefit. Sufficient leakage current paths are formed very quickly on the floor material surfaces during the spray process to allow charge transfer and limit significant voltage levels on the target subject. It was further found that respirable aerosols ingested into an air sampler were significantly reduced by spray charging. Uncharged levels of aerosols were over five times higher than that of charged during and after the spray session.

The addition of electrostatic charging to the spray tanning method as described by the present invention improves deposition efficiency and uniformity, which results in deeper tan color and realistic, long lasting tan characteristics. Since the cost of the tanning compounds are the largest per-session input for the tanning salon owner, the cost savings achieved with charged spray makes the electrostatic spray tanning methodology of the present invention more economically feasible than that of uncharged spray. The present invention reduces preferential deposits which can occur on body parts adjacent to directly-grounded plates meant to earth the human subjects of prior art systems. Another advantage provided by at least one embodiment of the present invention is that the costs associated with providing an apparatus for grounding the person to be coated during deposition of the coating material are eliminated. For example, eliminating the requirement for the use of a metal grounding plate allows the salon owner to avoid the maintenance and cleaning costs associated with insuring that a person standing on the grounding plate will have a sufficient electrical contact with a ground. In addition, elimination of the grounding plate removes the potential safety risk to the user of slipping and falling due to the requirement to stand upon a wet metal ground plate. Another advantage provided by embodiments of the present invention is that the use of an indirectly grounded surface coating, such as a dielectric material, on the spray booth floor allows for the implementation of a non-slip surface, thus improving the safety of the user as well as salon personnel.

Although the various embodiments of the present invention have been described for use in the application of tanning solutions to a human subject, it should be understood that the present invention can also be applied to other cosmetic spray applications, as well as for the application of medicinal and decontaminant sprays, for example, antibiotics, antitoxins, disinfectants, sanitizers, etc. It should also be understood that the various embodiments of the present invention can also be used for spraying other items, including animals or equipment.

Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions will fall within the scope and spirit of the disclosed invention as expressed in the claims.

The previous description is of a preferred embodiment for implementing the invention, and the scope of the invention should not necessarily be limited by this description. The scope of the present invention is instead defined by the following claims.

What is claimed:

1. An apparatus for electrostatically coating a body surface of a human target with a water-based coating composition, the apparatus comprising:
   an enclosure within which the human target is received, the enclosure including an electrically isolated floor system that is insulated from an electrical connection to either a voltage source or a ground reference, the electrically isolated floor system comprising an insulating base structure and a dielectric floor surface over the insulating base structure upon which the received human target stands and is electrically isolated from the ground reference;
   a mount positioned on the enclosure;
   an electrostatic nozzle connected to the mount for electrostatically spraying the water-based coating composition upon the body surface of the human target and dielectric floor surface of the enclosure;
   wherein the composition sprayed on the dielectric floor surface forms charge leakage paths from the body surface of the human target towards the ground reference.

2. The apparatus of claim 1, wherein a resistance of the charge leakage paths from the body surface to ground is less than 5000 Megaohms.

3. The apparatus of claim 1, wherein a resistance of the charge leakage paths from the body surface to ground is less than $80 \times 10^9$ ohms.

4. The apparatus of claim 1 wherein the enclosure comprises:
   a first wall wherein the mount is positioned on the first wall; and a second wall positioned substantially opposite the first wall, the second wall including a portion curved about an axis.

5. The apparatus of claim 4, wherein the portion of the second wall curved about an axis forms a parabolic curve.

6. The apparatus of claim 4, wherein the portion of the second wall curved about an axis forms an elliptical curve.

7. The apparatus of claim 4, wherein the portion of the second wall curved about an axis forms a circular curve.

8. The apparatus of claim 1, wherein the enclosure has a circular cross section corresponding to a vertical plane intersecting the enclosure.

9. The apparatus of claim 1, wherein the enclosure comprises:
a door for permitting the human to enter the enclosure.

10. The apparatus of claim 1, further comprising:
a fluid path connected to the electrostatic nozzle, the fluid path for carrying the water-based coating composition to the electrostatic nozzle.

11. The apparatus of claim 10, further comprising:
a reservoir connected to the fluid path, the reservoir for storing the water-based coating composition.

12. The apparatus of claim 1, wherein a vertical wall of the enclosure comprises a dielectric material.

13. The apparatus of claim 1, further comprising: means to electrically charge walls of the enclosure.

14. The apparatus of claim 1, wherein the electrostatic nozzle is configurable to pass an atomized and electrically charged water-based coating composition.

15. The apparatus of claim 1, further comprising an exhaust means placed proximate to the enclosure, the exhaust means for at least removing a portion of the water-based coating composition passed by the electrostatic nozzle.

16. The apparatus of claim 15, wherein the exhaust means comprises an exhaust fan.

17. The apparatus of claim 15, wherein the exhaust means is substantially formed of a dielectric material.

18. The apparatus of claim 1, wherein the mount comprises a mount moving means secured to the mount, wherein the mount is movable by the mount moving means such that the mount and the electrostatic nozzle are movable.

19. The apparatus of claim 18, wherein the mount moving means comprises a worm drive.

20. The apparatus of claim 18, wherein the mount moving means is configured to move the mount in a vertical direction.

21. The apparatus of claim 18, wherein the mount moving means is configured to pivot the mount in a vertical plane.

22. The apparatus of claim 18, wherein the mount moving means is configured to pivot the mount in a horizontal plane.

23. The apparatus of claim 1, wherein the electrostatic nozzle is a first electrostatic nozzle and the mount is a first mount, the apparatus further comprising:
a second mount positioned on the enclosure; and
a second electrostatic nozzle connected to the second mount, the second electrostatic nozzle for passing the water-based coating composition.

24. The apparatus of claim 23, wherein the second mount is located separate from the first mount.

25. The apparatus of claim 1, further comprising:
a misting chamber positioned adjacent to the enclosure, the misting chamber for substantially directing the water-based coating composition into the enclosure.

26. The apparatus of claim 1, further comprising:
a compressed air supply connected to the electrostatic nozzle, the compressed air supply for providing compressed air to the electrostatic nozzle.

27. The apparatus of claim 26, wherein the compressed air supply comprises an air compressor.

28. The apparatus of claim 26, wherein the compressed air supply comprises an air tank.

29. The apparatus of claim 26, further comprising:
an air flow regulator for regulating the pressure of the compressed air provided to the electrostatic nozzle.

30. The apparatus of claim 1, further comprising:
a conduit connected to the electrostatic nozzle, the conduit for receiving compressed air for use by the electrostatic nozzle.

31. The apparatus of claim 1, further comprising:
a reservoir for storing the water-based coating composition;
a coating composition line connected to the reservoir and the electrostatic nozzle, the coating composition line for carrying the water-based coating composition from the reservoir to the electrostatic nozzle.

32. An apparatus for electrostatically coating a body surface of a human target with a water-based coating composition, the apparatus comprising:
an enclosure within which the human target is received, the enclosure including an electrically isolating floor upon which the received human target stands and is electrically isolated from a ground reference, the electrically isolating floor being insulated from an electrical connection to either the ground reference or a voltage source;
a mount positioned on the enclosure;
an electrostatic nozzle connected to the mount for electrostatically spraying the water-based coating composition upon a body surface of the human target and floor of the enclosure;
wherein the composition sprayed on the floor surface forms charge leakage paths from the body surface of the human target such that accumulated charge on the body surface from electrostatic spraying is transferred from the body surface towards the ground reference.

33. The apparatus of claim 32, wherein the composition sprayed deposits charge onto the human target producing an elevated electrical potential on the human target which is insulated from the around reference by the electrically isolating floor.

34. The apparatus of claim 32, wherein a resistance of the charge leakage paths from the body surface to the ground is less than 5000 Megaohms.

35. The apparatus of claim 32, wherein a resistance of the charge leakage paths from the body surface to ground is less than $80 \times 10^9$ ohms.

36. The apparatus of claim 32, wherein the floor comprises a dielectric material surface over an insulated sump base for collecting sprayed coating composition.

37. The apparatus of claim 32, wherein the floor comprises a plastic encapsulated steel mesh floor over an insulated sump base for collecting sprayed coating composition.

38. The apparatus of claim 32, wherein the floor comprises a plate with no direct connection to ground over an insulated sump base for collecting sprayed coating composition.

39. The apparatus of claim 38, wherein the plate is comprised of dielectric material.

40. An apparatus for electrostatically coating a body surface of a human target with a water-based coating composition, the apparatus comprising:
an enclosure within which the human target is received;
a mount positioned on the enclosure;

an electrostatic nozzle connected to the mount, the electrostatic nozzle spraying the water-based coating composition for depositing upon the body surface of the human target; and an electrically insulating floor within the enclosure upon which the human target stands and is electrically isolated from a ground reference, the floor being insulated from an electrical connection to either the ground reference or a voltage source, and wherein the composition sprayed by the electrostatic nozzle deposits charge on the human target producing a transient elevated voltage on the human target that is isolated from ground by the electrically insulating floor.

41. The apparatus of claim 40, wherein the composition sprayed on the floor forms charge leakage paths from the body surface toward the ground reference.

42. The apparatus of claim 41, wherein a resistance from the body surface to the ground of the charge leakage paths is less than 5000 Megaohms.

43. The apparatus of claim 41, wherein a resistance from the body surface to the ground of the charge leakage paths is less than $80\times10^9$ ohms.

44. The apparatus of claim 40, wherein the floor comprises a dielectric material surface over an insulated sump base for collecting sprayed coating composition.

45. The apparatus of claim 40 wherein the floor comprises a plastic encapsulated steel mesh floor over an insulated sump base for collecting sprayed coating composition.

46. The apparatus of claim 40, wherein the floor comprises a plate which is electrically isolated from ground over an insulated sump base for collecting sprayed coating composition.

47. The apparatus of claim 46, wherein the plate is comprised of dielectric material.

* * * * *

UNITED STATES PATENT AND TRADEMARK OFFICE
CERTIFICATE OF CORRECTION

| | | |
|---|---|---|
| PATENT NO. | : 7,462,242 B2 | Page 1 of 1 |
| APPLICATION NO. | : 10/873838 | |
| DATED | : December 9, 2008 | |
| INVENTOR(S) | : Steven C. Cooper et al. | |

It is certified that error appears in the above-identified patent and that said Letters Patent is hereby corrected as shown below:

In the Specification:

At column 4, line numbers 53-54, please delete the words "over application" and replace with the word --overapplication--.

In the Claims:

At column 16, claim number 33, line number 43, please delete the word "around" and replace with the word --ground--.

Signed and Sealed this
Twenty-eighth Day of June, 2011

David J. Kappos
*Director of the United States Patent and Trademark Office*